(12) United States Patent
Shimada et al.

(10) Patent No.: US 8,486,039 B2
(45) Date of Patent: Jul. 16, 2013

(54) DISPOSABLE DIAPER

(75) Inventors: Takaaki Shimada, Kagawa (JP); Akiko Yagi, Kagawa (JP); Hideaki Maki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 403 days.

(21) Appl. No.: 12/742,723

(22) PCT Filed: Aug. 15, 2008

(86) PCT No.: PCT/JP2008/064629
§ 371 (c)(1),
(2), (4) Date: Aug. 23, 2010

(87) PCT Pub. No.: WO2009/063668
PCT Pub. Date: May 22, 2009

(65) Prior Publication Data
US 2010/0324519 A1    Dec. 23, 2010

(30) Foreign Application Priority Data

Nov. 15, 2007    (JP) .................................. 2007-297302

(51) Int. Cl.
*A61F 13/15*    (2006.01)
*A61F 13/20*    (2006.01)

(52) U.S. Cl.
USPC ............. 604/385.27; 604/385.24; 604/385.29

(58) Field of Classification Search
USPC .............. 604/385.24–385.31, 385.01, 385.16
See application file for complete search history.

(56) References Cited

U.S. PATENT DOCUMENTS

| 5,968,029 | A  | * | 10/1999 | Chappell et al. ......... 604/385.23 |
| 6,602,238 | B2 | * | 8/2003  | Takei et al. ............... 604/385.26 |
| 7,727,214 | B2 | * | 6/2010  | Torigoshi et al. ........ 604/385.28 |
| 2003/0139726 | A1 | * | 7/2003 | Gibbs ....................... 604/385.29 |
| 2004/0030317 | A1 | * | 2/2004 | Torigoshi ................. 604/385.27 |
| 2004/0133180 | A1 | * | 7/2004 | Mori et al. ............... 604/385.25 |

(Continued)

FOREIGN PATENT DOCUMENTS

| EP | 1 621 168 A1 | 2/2006 |
| JP | 2002-248127  | 9/2002 |

(Continued)

OTHER PUBLICATIONS

International Search Report from corresponding PCT application No. PCT/JP2008/064629, dated Nov. 25, 2008, 2 pages.

(Continued)

*Primary Examiner* — Michele M Kidwell
(74) *Attorney, Agent, or Firm* — Brinks Hofer Gilson & Lione

(57) ABSTRACT

The present invention provides a disposable diaper which prevents body waste from leaking sideways without sacrificing a bodily fluid absorbing capacity of a liquid-absorbent structure and to assure a high retention for urine and discharged feces. The waist elastic members includes first and second waist elastic members wherein elastic members extend in the transverse direction across opposite lateral regions so as not to present in central zones of front and rear waist regions. The second waist elastic members in the front waist region extend from transverse opposite side edges of the front waist region in the transverse direction beyond transverse opposite side edges of a liquid-absorbent core while the second elastic members in the rear waist region extend from transverse opposite side edges in the transverse direction and terminate short of the side edges of the core.

12 Claims, 5 Drawing Sheets

U.S. PATENT DOCUMENTS

| | | | |
|---|---|---|---|
| 2004/0243083 A1* | 12/2004 | Matsuda et al. | 604/385.01 |
| 2005/0107763 A1* | 5/2005 | Matsuda et al. | 604/396 |
| 2006/0200109 A1 | 9/2006 | Oba et al. | |

FOREIGN PATENT DOCUMENTS

| | | |
|---|---|---|
| JP | 2004-049765 | 2/2004 |
| JP | 2004-236832 | 8/2004 |
| JP | 2007-029507 | 2/2007 |

OTHER PUBLICATIONS

European Supplemental Search Report from corresponding EP application No. 08850113.5, dated Dec. 10, 2012 8 pages.

* cited by examiner

DISPOSABLE DIAPER

RELATED APPLICATION

This application is a 35 U.S.C. §371 national phase filing of International Patent Application No. PCT/JP2008/064629, filed Aug. 15, 2008, through which and to which priority is claimed under 35 U.S.C. §119 to Japanese Patent Application No. 2007-297302, filed Nov. 15, 2007.

TECHNICAL FIELD

The present invention relates to a disposable diaper and particularly to a disposable diaper adapted to prevent bodily fluids from leaking sideways and to protect the wearer's body from soiling due to defecation without sacrificing a desired absorption capacity.

RELATED ART

There have already been proposed disposable diapers provided in a front waist region as well as in a rear waist region with a plurality of elastic members circumferentially extending therein so that these elastic members may serve to improve a fit of the diaper to the wearer's body. For example, JP 2002-248127A cited herein discloses a disposable diaper comprising an absorbent structure extending across a crotch region and further extending into front and rear waist regions and a plurality of elastic members extending from transversely opposite side edges of the respective waist regions to at least outer side edges of the absorbent structure in a transverse direction.
PATENT DOCUMENT 1: JP 2002-248127A

DISCLOSURE OF THE INVENTION

Problem to be Solved by the Invention

The elastic members associated with the waist regions in the diaper disclosed by JP 2002-248127A comprise a plurality of elastic members circumferentially extending completely along respective waist-opening peripheries of the front and rear waist regions and a plurality of elastic members extending from the side edges of the respective waist regions to the side edges of the absorbent structure. In this way, a tensile stress of the waist elastic members is exerted on the side edges of the absorbent structure so as to improve a fit of the absorbent structure to the wearer's body.

However, the side edges of the absorbent structure are put in close contact with the wearer's body under the tensile stress of the elastic members in the rear waist region in the same manner as in the front waist region. As a result, it is difficult to leave a clearance gap between the wearer's body and the absorbent structure and it is still more difficult to assure a space sufficiently large to receive and retain discharged feces without spreading the latter. Eventually, such discharged feces may come in contact with the wearer's buttock, soil the wearer's skin and/or cause eruption.

The present invention provides a disposable diaper improved so that, in the front waist region, the fit of the liquid-absorbent structure to the wearer's body is ensured so as to prevent bodily fluids from leaking sideways but not to deteriorate the bodily fluid absorbing capacity of the liquid-absorbent core and, in the rear waist region, it is assured to leave between the wearer's buttock and the bodily fluid absorbent structure a space adapted to receive and retain discharged feces without spreading the latter.

Measure to Solve the Problem

According to the present invention, there is provided a disposable diaper comprising a chassis having a longitudinal direction, a transverse direction, a side facing the wearer's skin and a side facing away from the wearer's skin and configurationally comprising a front waist region, a rear waist region, a crotch region extending between the front and rear waist regions, a waist-opening and a pair of leg-openings, a liquid-absorbent structure provided on the side facing the wearer's skin of the chassis and extending across the crotch region further into the front and rear waist regions, the liquid-absorbent structure containing therein a liquid-absorbent core, and, a plurality of waist elastic members extending under tension in the transverse direction.

The present invention is characterized in that the waist elastic members comprise first waist elastic members extending in a transverse direction in a vicinity of the waist-opening periphery and second waist elastic members provided between the leg-openings peripheries and the first waist elastic members and extending in the transverse direction across opposite lateral regions so as not to be present in central zones of the front and rear waist regions, and the second waist elastic members in the front waist region extend from transversely opposite side edges of the front waist region in the transverse direction beyond transversely opposite side edges of the liquid-absorbent core while the second waist elastic members in the rear waist region extend from transversely opposite side edges in the transverse direction and terminate short of the side edges of the liquid-absorbent core.

The present invention may be implemented also in preferred embodiments as follow:

(1) The dimension in the transverse direction between the inner end portions of the second waist elastic members and the side edges of the liquid-absorbent core in the front waist region is in a range of about 10 to 30% of the dimension in the transverse direction of the liquid-absorbent core and the dimension in the transverse direction between the inner end portions of the second waist elastic members and the side edges of the liquid-absorbent core in the front waist region is about 10% or less.

(2) The rear end of the liquid-absorbent core is spaced from the region of the first waist elastic members closest to said rear end.

(3) The chassis includes a sheet lying on a side of the second waist elastic members facing away from the wearer's skin and the inner end portions of the second waist elastic members are permanently bonded to said sheet.

(4) Said sheet is formed of a moisture-permeable plastic film and has a thickness in a range of about 0.015 to 0.05 mm.

Effect of the Invention

According to the present invention, in the front waist region, the second waist elastic members extend from the side edges of the front waist region across the side edges of the liquid-absorbent structure to the side edges of the liquid-absorbent core. In the rear waist region, the second waist elastic members extend from the side edges of the rear waist region and terminate short of the side edges of the liquid-absorbent structure, i.e., do not extend to the liquid-absorbent core. With such arrangement, in the front waist region, the tensile stress of the second waist elastic members affects the liquid-absorbent core at a degree not deteriorating the bodily fluid absorbing capacity of the liquid-absorbent core and puts the liquid-absorbent core in close contact with the wearer's body. In the rear waist region, the tensile stress of the second waist elastic members should not directly affect the liquid-absorbent structure so as to put this liquid-absorbent structure in excessively close contact with the wearer's skin. Consequentially, a space sufficiently large to retain the discharged feces without spreading this is assured between the wearer's body and the bodily fluid absorbent structure. In this way, a high retention capability for body waste is obtained.

Figure 1:
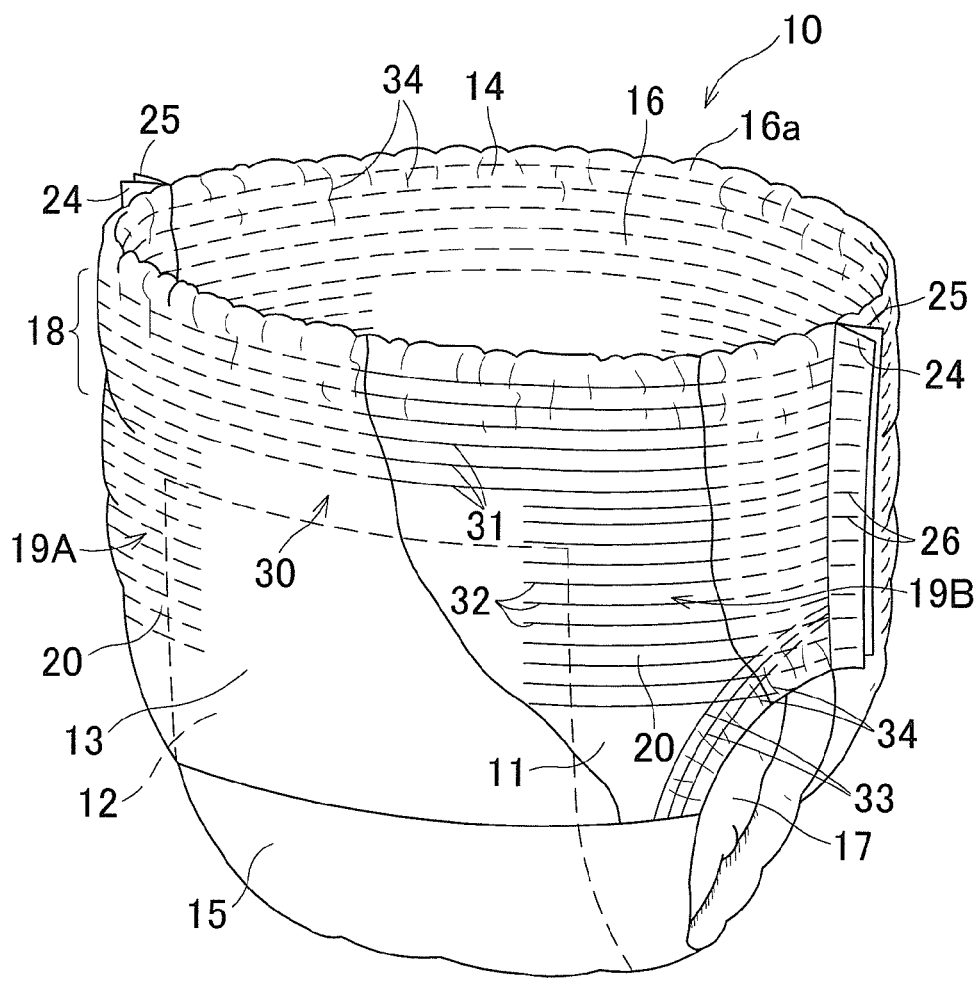
FIG. 1 is a partially cutaway perspective view of a first embodiment of the diaper according to the invention.
Figure 1:
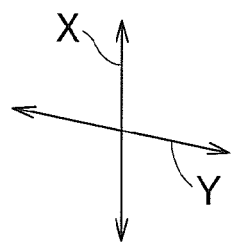

IDENTIFICATION OF REFERENCE NUMERALS USED IN THE DRAWINGS 10 disposable diaper
11 chassis
12 liquid-absorbent structure
12c side edges of liquid-absorbent structure
13 front waist region
14 rear waist region
15 crotch region
16 waist-opening
16a waist-opening periphery
17 leg-openings
18 upper elasticized region
19 lower elasticized region
20 side edges of front and rear waist regions
24 side edges of front waist region
25 side edges of rear waist region
30 non-elasticized region
31 first waist elastic member
31a region of first waist elastic member placed aside closely toward rear end of liquid-absorbent core
32 second waist elastic member
33 leg elastic members
38 inner end of second waist elastic member
44 liquid-absorbent core
44c side edges of liquid-absorbent core
70 (fixing) sheet
D1 dimension as measured in transverse direction between inner end of second waist elastic member and associated side edge of liquid-absorbent core in rear waist region
L1 dimension as measured in transverse direction between inner end of second waist elastic member and associated side edge of liquid-absorbent core in front waist region
L2 dimension of liquid-absorbent core as measured in transverse direction
W dimension of liquid-absorbent structure as measured in transverse direction
X longitudinal direction
Y transverse direction

DESCRIPTION OF THE BEST MODE FOR WORKING OF THE INVENTION

FIGS. 1 through 4 illustrate a first embodiment of the present invention on its second aspect. FIG. 1 is a partially cutaway perspective view of a diaper 10 as put on the wearer's body. Referring to FIG. 1 showing the diaper 10 put on the wearer's body wherein a longitudinal direction is designated by X and a transverse direction is designated by Y.

As will be seen in FIG. 1, the diaper 10 comprises a chassis 11 and a liquid-absorbent structure 12 attached to the inner side of the chassis 11, i.e., the side of the chassis 11 facing the wearer's skin and extending in the longitudinal direction X. The diaper 10 configurationally comprises a front waist region 13, a rear waist region 14 and a crotch region 15 extending between these two waist regions. Each of the front and rear waist regions 13, 14 is sectionalized into an upper elasticized region 18, lower elasticized regions 19A, 19B and a non-elasticized region 30 extending between the lower elasticized regions 19A, 19B. The upper elasticized region 18 is provided with a plurality of first waist elastic member 31 extending along a waist-opening periphery 16a in the transverse direction Y and the lower elasticized regions 19A, 19B are respectively provided with a plurality of second waist elastic member 32 extending in the transverse direction Y across opposite lateral regions 20 of each waist region 13, 14.

Figure 2:
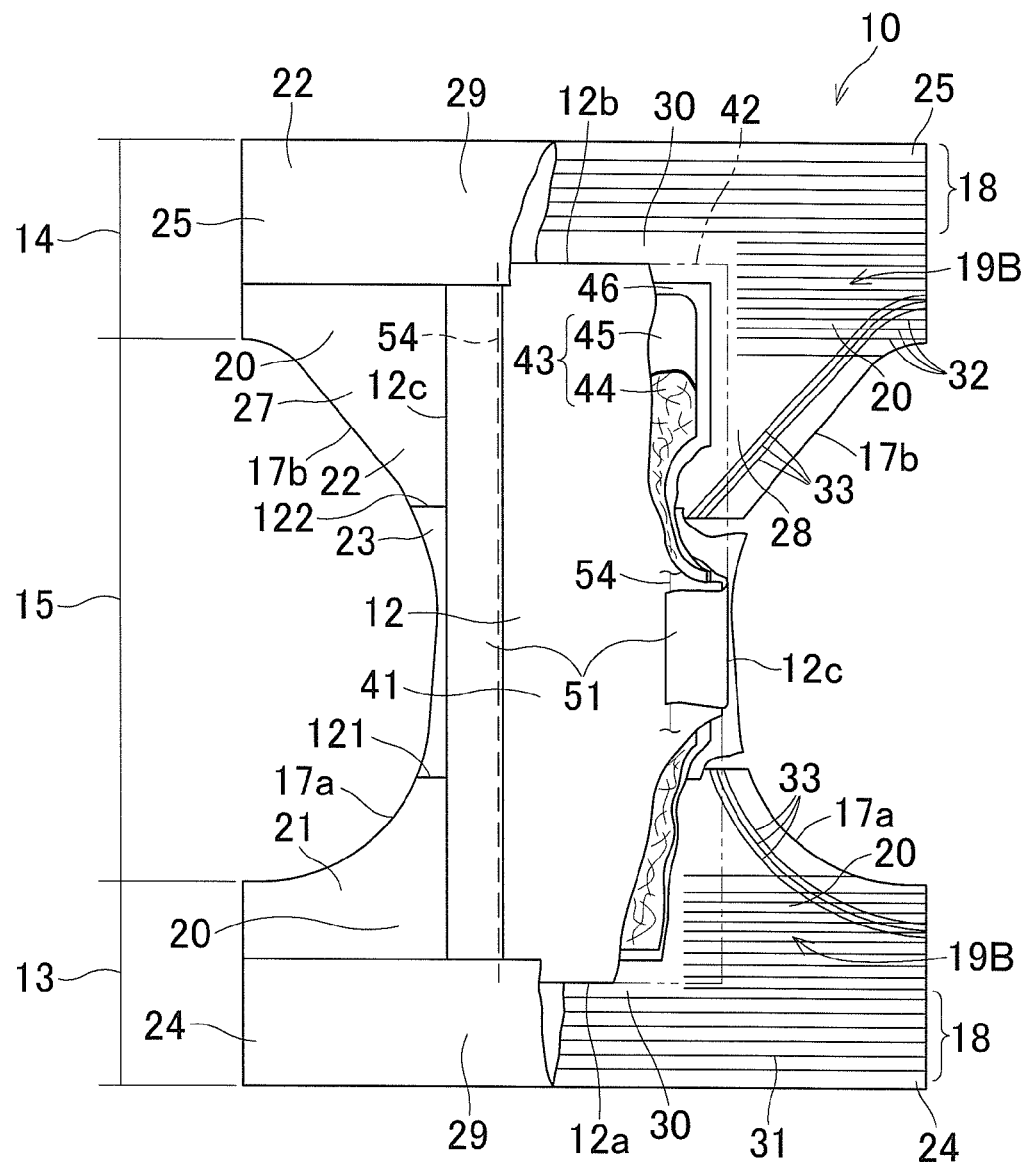
FIG. 2 is a developed plan view of the diaper.
Figure 3:
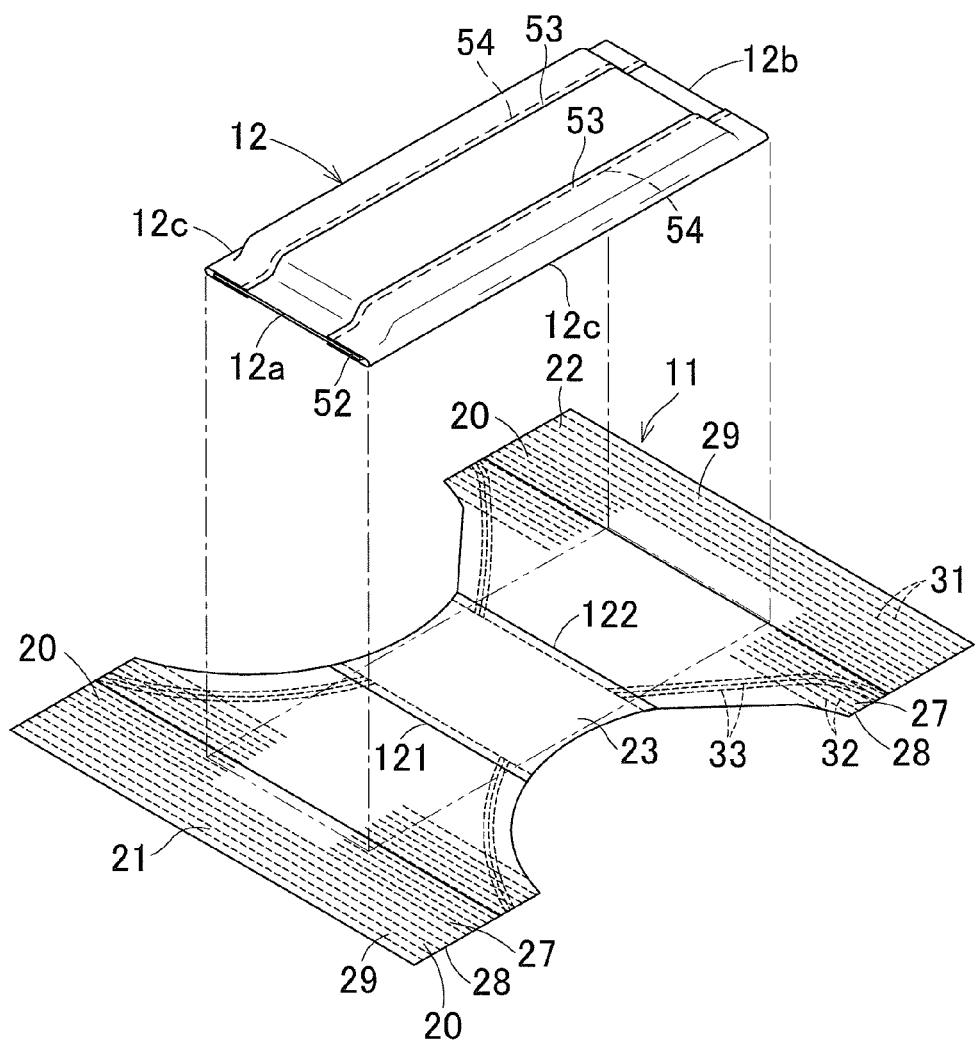
FIG. 3 is an exploded perspective view of the diaper.

FIG. 2 is a developed plan view of the diaper 10 as the front and rear waist regions 13, 14 have been separated from each other along respective seams 26 and developed in the longitudinal direction X as well as in the transverse direction Y and FIG. 3 is an exploded perspective view of the diaper 10 as the chassis 11 and the liquid-absorbent structure 12 have been separated from each other.

The chassis 11 comprises a substantially trapezoidal front member 21 including the front waist region 13, a substantially trapezoidal rear member 22 including the rear waist region 14 and a substantially rectangular intermediate member 23 extending between the front member 21 and the rear member 22 and including the crotch region 15. These front member 21, intermediate member 23 and the rear member 22 are arranged in the longitudinal direction X in this order and joined together along joint lines 21, 22. Respective pairs of transversely opposite side edges 24, 25 of the front member 21 and the rear member 22 are put flat and bonded together at seams 26 arranged intermittently in the longitudinal direction X by means of, for example, hot melt adhesive, heat embossing, sonic or heat sealing technique, whereupon a waist-opening 216 and a pair of leg-openings 17 are defined. The transversely opposite side edges 24 are provided on the (See FIG. 1).

The front member 21, the intermediate member 23 and the rear member 22 are formed by a liquid-pervious inner layer sheet 27 facing the wearer's skin and a liquid-impervious outer layer sheet 28 facing away from the wearer's skin joined to each other. Both the inner layer sheet 27 and the outer layer sheet 28 are formed from an air-permeable fibrous nonwoven fabric. The outer layer sheet 28 extends in the longitudinal direction X beyond longitudinally opposite ends of the inner layer sheet 27. After the liquid-absorbent structure 12 has been placed on the inner side of the chassis 11, the portions 29 of the outer layer sheet 28 extending outward beyond the opposite ends of the inner layer sheet 27 in this manner are folded back toward the liquid-absorbent structure 12 so as to cover front and rear ends 12a, 12b of the liquid-absorbent structure 12 and bonded thereto at the respective pairs of side edges 24, 25. The portions 29 of the outer layer sheet 28 covering the front and rear ends 12a, 12b of the liquid-absorbent structure 12 from above function as leak-barrier walls preventing body waste from leaking out even if any amount of bodily fluids which has not been absorbed by the liquid-absorbent structure 12 leaks beyond the front and rear ends 12a, 12b.

Between the inner layer sheet 27 and the outer layer sheet 28, the first waist elastic members 31, the second waist elastic members 32 and a plurality of leg elastic members 33 extending along upper and lower halves 17a, 17b of the respective leg-openings' peripheries are sandwiched. These elastic members 31, 32, 33 are attached under tension at least to the inner layer sheet 27 of the inner layer sheet 27 and outer layer sheet 28 by means of hot melt adhesive (not shown). A plurality of gathers 34 appear in the chassis 211 under contraction of these elastic members 31, 32, 33 (See FIG. 1).

The liquid-absorbent structure 12 has a substantially rectangular shape and comprises a liquid-pervious inner sheet 41, a liquid-impervious outer sheet 42 and a liquid-absorbent core assembly 43 interposed between these two sheets. The inner sheet 41 and the outer sheet 42 extend outward beyond a peripheral edge of the substantially rectangular core assembly 43 and the portions of these sheets 41, 42 extending outward beyond the periphery of the core assembly 43 are put flat and bonded together by means of hot melt adhesive (not shown) to define the front end 12a opposed to the front end of the chassis 11, the rear end 12b opposed to the rear end of the chassis 11 and a pair of opposite side edges 12c extending between the front and rear ends 12a, 12b in the longitudinal direction X. The front end 212a and the rear end 12b are bonded to the inner layer sheet 27 in the front member 21 and to the inner layer sheet 27 in the rear member 22, respectively, by means of hot melt adhesive (not shown).

The core assembly 43 comprises a rectangular liquid-absorbent core 44 formed by a mixture of fluff pulp, super-absorbent polymer particles and, if desired, heat-sealable staple fibers and a liquid-spreadable shape retaining sheet 45 such as tissue paper with which the core 44 is wrapped. Between the outer sheet 42 and the core assembly 43, a liquid-barrier sheet 46 formed from a liquid-impervious and moisture-permeable plastic film is interposed. A size of the liquid-barrier sheet 46 is sufficient to cover most part of the bottom face of the core assembly 43 and preferably covers the entire bottom face of the core assembly 43 in order to ensure a sufficient leak-barrier effect.

A pair of barrier cuffs 51 each formed from a liquid-impervious sheet and extending in the longitudinal direction X are attached to the opposite side edges 12c of the liquid-absorbent structure 12. Each of these barrier cuffs 51 has a fixed edge 52 fixed between the associated side edge 12c of the liquid-absorbent structure 12 and the chassis 11 so as to intersect with the innermost segment of the associated leg elastic members 33 and a free edge 53 collapsed toward the side of the liquid-absorbent core 44 wherein at least one elastic member 54 extending in the longitudinal direction X is attached to the inner surface of the free edge 53. With the diaper 10 put on the wearer's body, the free edge 53 is spaced upward from the inner sheet 41 under contraction of the elastic member 54 and thereby completely covers the associated side edge 12c of the liquid-absorbent structure 12 to prevent any amount of body waste from leaking sideways. In the crotch region 15, the elastic member 54 extends in the longitudinal direction X and cooperates with the leg elastic members 33 extending along the upper and lower halves 17a, 17b of the associated leg-opening 17 to define an imaginary annular elasticized region along this leg-opening 17. In this way, the imaginary annular elasticized regions surround the wearer's legs (not shown) and thereby prevent leak of body waste from occurring around the wearer's legs.

Figure 4A:
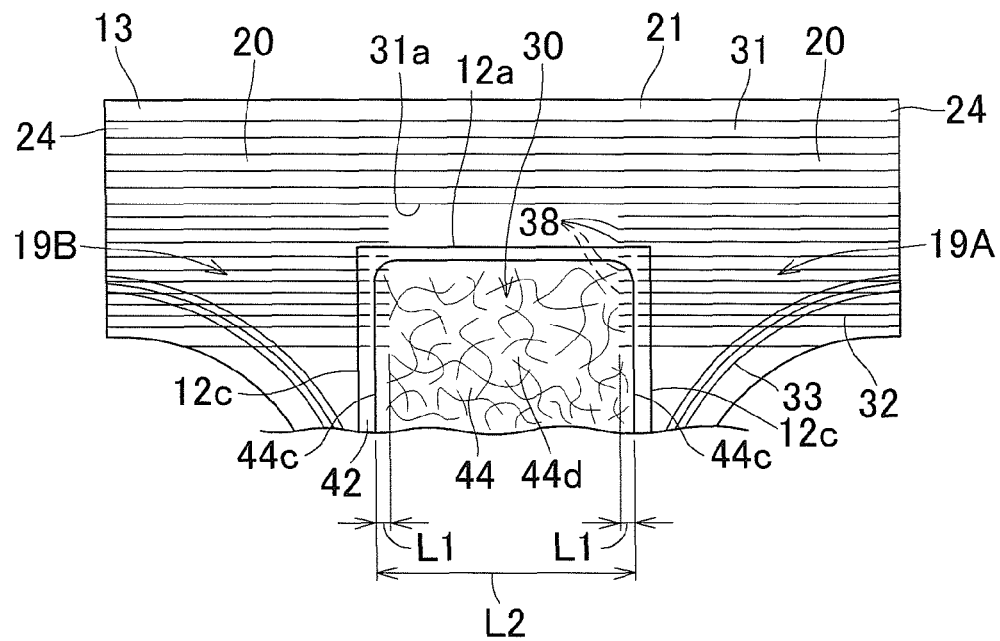
FIG. 4 shows a front member of the diaper in a partially scale-enlarged view A and a rear member of the diaper in a partially scale-enlarged view B.

FIG. 4A is a partially scale-enlarged diagram illustrating the front member 21 which has been illustrated also on FIG. 2 in the developed plan view of the diaper 10. For convenience of illustration, the inner layer sheet 27, the liquid-barrier sheet 46, the shape retaining sheet 45 and the inner sheet 41 are eliminated in FIG. 4.

As will be apparent from FIG. 4A, the second waist elastic members 32 extend from the side edges 24 toward the liquid-absorbent structure 12 and extend inward slightly beyond the side edges 12c of the liquid-absorbent structure 12 to the side edges 44c of the core 44. The second waist elastic members 32 extend in this manner to the side edges 44c of the core 44 but not to the central zone 44d of the core 44 so that the core 44 as a whole is substantially free from any affection due to contraction of the second waist elastic members 32 and, in consequence, the liquid-absorbent structure 12 is able to maintain not only its bodily fluid absorbing capacity but also its fit to the wearer's body.

Assumed that the second waist elastic members 32 extend under tension across the liquid-absorbent structure 12 in the transverse direction Y, the liquid-absorbent structure 12 will be affected by contraction of the second waist elastic members 32 and the core 44 as a whole will get wrinkled, resulting in that the bodily fluid absorbing capacity of the core 44 should be significantly deteriorated. On the contrary, when the second waist elastic members 32 extend from the respective pairs of opposite side edges 24, 25 of the front and rear waist regions 13, 14 and terminate short of the side edges 12c of the liquid-absorbent structure 12, i.e., the second waist elastic members are not present on the core 44, the tensile stress of the second waist elastic members 32 should excessively affect the liquid-absorbent structure 12 and therefore the core 44 should not get wrinkles.

However, if the liquid-absorbent structure 12 is bonded to the inner surface of the chassis 11 only at the front and rear ends 12a, 12b and the tensile stress of the second elastic members 32 is not exerted on the liquid-absorbent structure 12, the liquid-absorbent structure 12 should be forced up forward together with the wearer's front waist region as the wearer bends him- or herself forward and consequently the liquid-absorbent structure 12 should be slipped up from the desired position. In order to avoid such displacement of the liquid-absorbent structure 12, it may be contemplated to coat the large surface of the liquid-absorbent structure 12 facing away from the wearer's skin and facing the chassis 11 with adhesive. In this case, the moisture-permeability of the diaper 10 as a whole is deteriorated and the interior of the diaper becomes stuffy. This is undesirable from the hygiene viewpoint.

To overcome this problem, in the front waist region 13, the second waist elastic members 32 extend to the side edges 44c of the liquid-absorbent core 44 and not to the central zone 44d of the liquid-absorbent core 44 so that the absorbing capacity of the core 44 may be substantially not affected by the second waist elastic members 32. The central zone 44d of the core 44 is not affected by contraction of the second waist elastic members 32 and therefore not apt to get wrinkles. In this way, the absorbing capacity of the core 44 is substantially not deteriorated. On the other hand, the side edges 44c are put in close contact with the wearer's body under the tensile stress of the second waist elastic members 32 and thereby any displacement of the liquid-absorbent structure 12 is also restrained.

To achieve such effect, a distance L1 in the transverse direction Y between the side edges of the core 44 and the associated inner end portions 38 of the second waist elastic members 38 is preferably about 10 to 30% of a dimension L2 in the transverse direction Y of the liquid-absorbent core 44. If the distance L1 is about 30% or more of the dimension L2 in the transverse direction Y of the liquid-absorbent core 44, the core 44 will get wrinkles over a relatively large area under contraction of the second waist elastic members 32, resulting in deterioration of the bodily fluid absorbing capacity of the core 44 and occurrence of liquid leak. If the distance L1 is less than 10% of the dimension L2 in the transverse direction Y of the liquid-absorbent structure 12, the tensile stress of the second waist elastic members 32 will not effectively function to put the liquid-absorbent structure in close contact with the wearer's body, resulting in that a clearance gap will be formed between the liquid-absorbent structure 12 and the wearer's body and bodily fluids should leak out through such clearance gap.

Figure 4B:
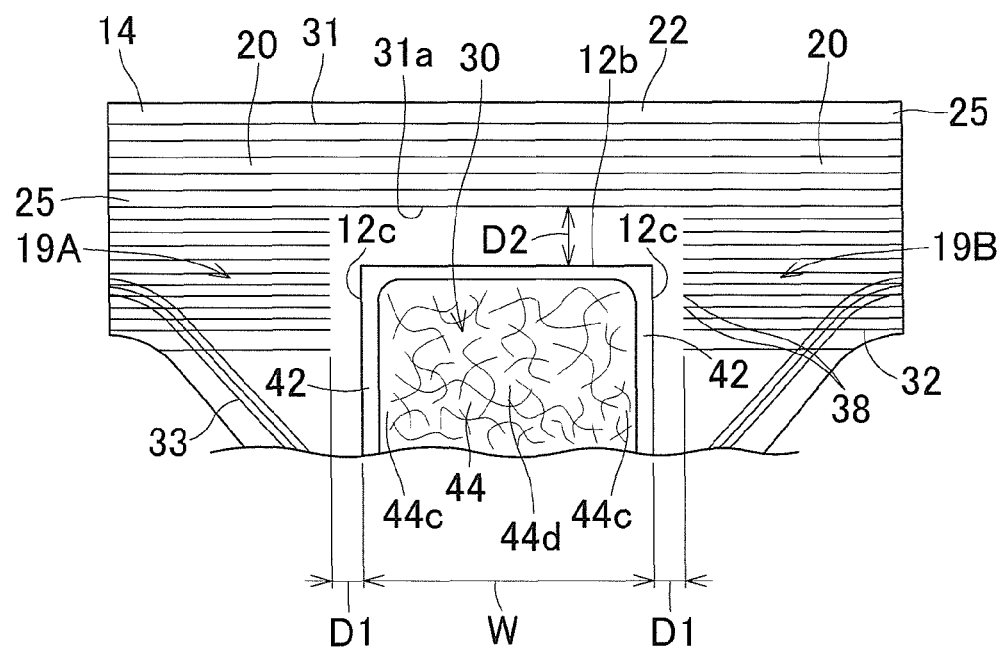

FIG. 4B is a partially scale-enlarged diagram illustrating the rear member 22 which has been illustrated also by FIG. 2 in the developed plan view of the diaper 10. For convenience of illustration, the inner layer sheet 27, the liquid-barrier sheet 46, the shape retaining sheet 45 and the inner sheet 41 are eliminated in FIG. 4 as is the case with FIG. 4A.

Referring to FIG. 4B, the second waist elastic members 32 extend from the side edges 25 of the rear member 22 in the transverse direction Y and terminate short of the side edges 12c of the liquid-absorbent structure 12. Unlike in the front member 21, the second waist elastic members 32 do not extend to the liquid-absorbent structure 12 and, in consequence, the liquid-absorbent structure 12 is substantially not affected by contraction of the second waist elastic members 32. In this way, between the liquid-absorbent structure 12 and the wearer's buttock, the space to retain discharged feces without spreading this can be assured.

Assumed now that, similar to the case of the front waist region 13, the second waist elastic members 32 extend in the transverse direction Y slightly beyond the side edges 12c of the liquid-absorbent structure 12 in the rear waist region 14 also, the liquid-absorbent structure 12 as a whole will be put in close contact with the wearer's buttock and it will be difficult to assure the space to retain discharged feces. As a result, the discharged feces will be squeezed between the liquid-absorbent structure 12 and the wearer's buttock and the feces will soil the wearer's skin or leak out from the diaper. However, in the rear waist region 14 according to this embodiment of the invention, the affection due to contraction of the second waist elastic members 32 is minimized so that the liquid-absorbent structure 12 is not put in excessively close contact with the wearer's buttock and the space of an appropriate size to retain the discharged feces is defined between the buttock and the liquid-absorbent structure 12.

In the rear waist region 14, a distance D1 in the transverse direction Y between the inner ends 38 of the second waist elastic members 32 and the side edges 12c of the liquid-absorbent structure 12 is preferably less than 10% of a dimension W in the transverse direction Y of the liquid-absorbent structure 12. This is for the reason that, if the distance D1 is about 10% or more of the dimension W in the transverse direction Y of the liquid-absorbent structure 12, the fit of the liquid-absorbent structure 12 to the wearer's body will be seriously deteriorated and the space defined between the liquid-absorbent structure 12 and the wearer's buttock will become relatively large, causing a problem that body waste should leak out from the diaper.

While the second waist elastic members 32 may be formed by placing the elastic members each previously extended to the predetermined dimension on transversely opposite lateral portions of the front and rear members 21, 22, it is also possible to form these second waist elastic members 32 by bonding the second waist elastic members 32 under tension in the transverse direction Y and then removing portions of the second waist elastic members 32 lying in a desired range in the vicinity of the central zones of the front and rear waist regions 13, 14 (at least a range opposed to the central zone 44d of the core 44) or using said desired range as a adhesion-free zone and partially cutting this adhesion-free zone so as to snap back this adhesion-free zone (i.e., causes such free zone to contract by itself to the vicinity of the bonded portions of the second waist elastic members 32). In general, during a process for making the disposable diaper, the components such as sheet members and elastic members are successively overlapped one on another in a given direction to assemble these components. In view of this, the latter procedure is preferred.

Between the lower elasticized regions 19A, 19B in the front and rear waist regions 13, 14, the non-elasticized regions 30 including none of the second waist elastic members 32 extending therein is not limited to the regions opposed to the core 44 and present outside the front and rear ends 12a, 12b of the liquid-absorbent structure 12 as viewed in the longitudinal direction X. As has previously been described, not only in the rear member 23 but also in the front member 21, it is essential to alleviate the tensile stress of the second waist elastic members 32 exerted on the central zone 44d of the core 44 and thereby to maintain the body fluid absorbing capacity thereof. Specifically, the portions of the second waist elastic members 32 lying outside the front and rear ends 12a, 12b as viewed in the longitudinal direction X may be cut to ensure that the front and rear ends 12a, 12b are sufficiently spaced from the elastic members closest thereto in the longitudinal direction X (the lowermost elastic member 31a of the first waist elastic members in FIGS. 4A and 4B). In consequence, the affection due to contraction of the second waist elastic members 32 can be alleviated. A distance D2 between the rear end 12b of the liquid-absorbent structure 12 and the elastic member 31a is preferably equal to or larger than a distance D1 between the inner end portion 38 of the second waist elastic members 32 and the side edges 12c of the liquid-absorbent structure 12 as viewed in the transverse direction Y. In this case, around the rear end 12b of the liquid-absorbent structure 12, a non-elasticized region having a desired size is defined and allows the discharged feces to be reliably retained.

Figure 5:
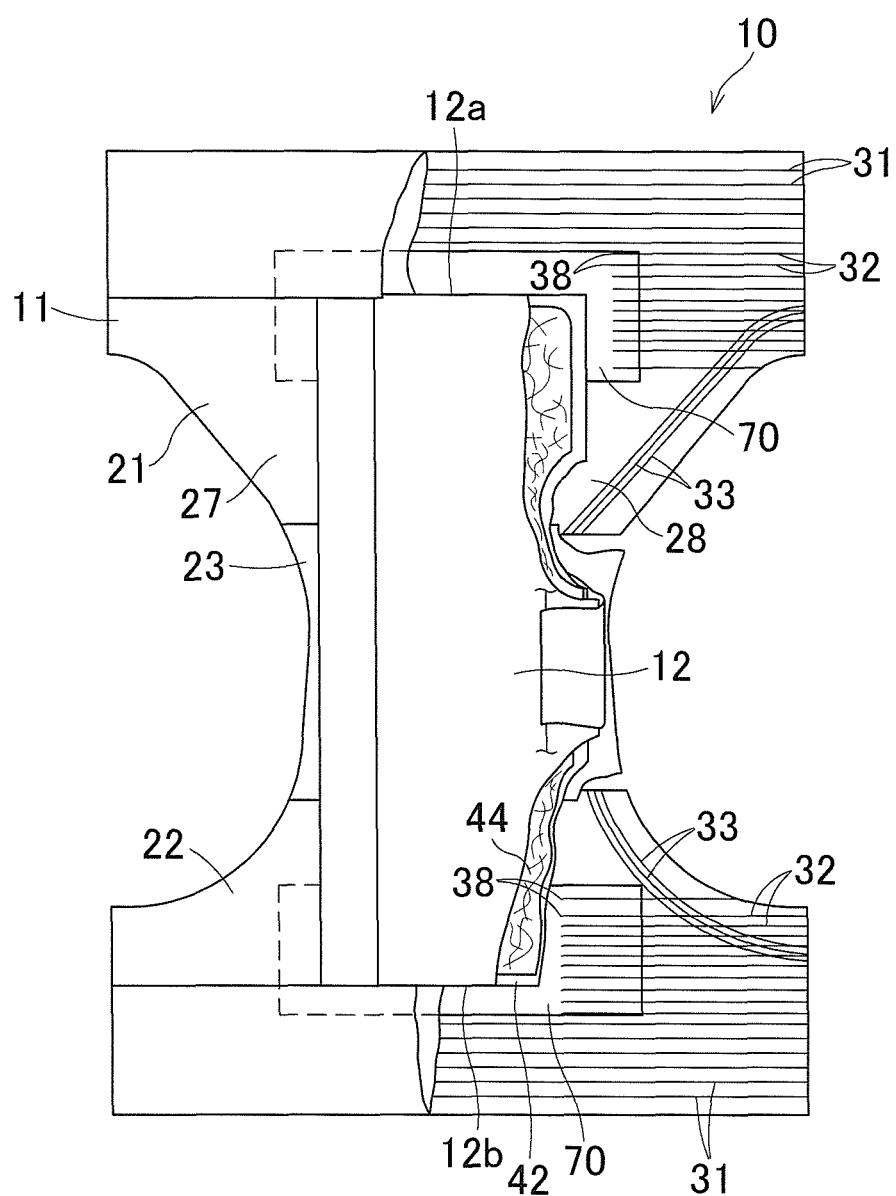
FIG. 5 is a partially cutaway perspective view of the second embodiment of the diaper according to the invention.

FIG. 5 is a partially cutaway developed plan view showing a second embodiment of the diaper 10 according to the present invention on its second aspect. The diaper 10 according to the second embodiment is basically similar to the first embodiment and therefore only the feature distinguished from the first embodiment will be described here.

Referring to FIG. 5, substantially rectangular moisture-permeable fixing sheets 70 is interposed between the inner layer sheet 27 and the outer layer sheet 28 at a position opposed to the front and rear ends 12a, 12b of the liquid-absorbent structure 12 and bonded to at least respective inner surfaces of the inner layer sheets 27. The inner ends 38 of the second waist elastic members 32 interposed between the inner and outer layer sheets 27, 28 and the vicinity thereof are interposed between the inner layer sheet 27 and the fixing sheets 70 and permanently bonded to the both sheets 27, 70.

While, in many cases, the elastic members are permanently bonded to the sheet members by means of adhesive of well known type such as hot melt adhesive, when the end portions of the elastic members must be bonded under tension to the sheet member as in the case of the second waist elastic members 232, it is required to coat these end portions and the vicinity thereof with much more amount of adhesive than the other joint regions in order to prevent some of the elastic members from falling off during the process of making the diaper or use of the diaper. The regions coated with excessive amount of adhesive inevitably become hardened and deteriorate a unique texture of the fibrous nonwoven fabric, eventually creating a feeling of discomfort against the wearer. In addition, in the case of the diaper in which the outer surface of the outer layer sheet 228 is printed with a figure or a pattern for decorative effect, the regions excessively coated with adhesive may be seen through from the exterior and such decorative effect may be seriously affected.

In the present embodiment, however, the fixing sheets 70 is interposed between the inner and outer layer sheets 27, 28 so as to cooperate with the inner layer sheet 27 to interpose the inner end portions 38 as the joint ends of the second waist elastic members 32. With such arrangement, even if the inner end portions 38 has been coated with a large amount of adhesive, the outer sheet 28 should not be partially hardened and the texture thereof should not be deteriorated. In the course of making the diaper 10, the regions in which the fixing sheets 70 are provided has its thickness as well as stiffness increased in comparison to the other regions. In consequence, the regions of the fixing sheets 70 can be efficiently press-processed and thereby the inner end portions 38 and the vicinity thereof can be further firmly bonded between the inner sheet 27 and the fixing sheets 70. The inner end portions 38 and the vicinity thereof may be further firmly bonded in this way to decrease the amount of adhesive to be used.

The fixing sheet 70 is made of moisture-permeable plastic film or nonwoven fabric and preferably has a thickness in a range of about 0.015 to 0.05 mm. The fixing sheet 70 may have a size at least covering the inner end portion 38 of the second waist elastic member 32 plus about 1 to 20 mm around the end portion 38. The shape of fixing sheet 70 is not limited to the substantially rectangular shape as illustrated, but may have other various shapes as circular or polygonal shape.

It is also possible to interposed two fixing sheets 70 are interposed between the inner and outer layer sheets 27, 28 so as to interpose the inner end portions 38 of the second waist elastic members 32 and the vicinity thereof from above and below. In the case of the fixing sheet 70 comprises upper and lower sheets, the adhesive used to fix the inner end portions 38 and the vicinity thereof may be coated on opposed inner surfaces of these two fixing sheets 70 and consequentially there is no anxiety that the inner layer sheet 27 and the outer layer sheet 28 might be partially hardened due to the presence of the adhesive.

The fixing sheet 70 may be provided with a decorative figure or pattern adapted to be seen through from the exterior by means of printing or the other technique.

The first and second waist elastic members 31, 32, the leg elastic members 33 and elastic members 254 are made of natural or synthetic rubber and implemented in the form of strings or ribbons. The second waist elastic members 32 preferably exhibit a tensile stress in a range of about 0.5 to 2.5 N/25 mm at an extending ratio of about 80%.

The tensile stress values of the second waist elastic members 232 are measured by a method as will be described below.

First, the diaper is developed as seen in FIG. 2 and the second waist elastic members 32 are extended. Test pieces each having a width of about 25 mm for the second waist elastic members 32 are cut away from the diaper 10 in this extended state and this length of about 25 mm is the maximum extended length. The test piece is held by chucks of a contractile strength tester and subjected to 1 cycle test with a moving velocity of 100 mm/min and an inversion distance corresponding to 90% of the maximum extended length of the test piece. A tensile stress after inversion is measured at a point the length of the test piece reaching 80% of its maximum extended length. It should be noted that a distance between the chucks should be appropriately changed depending on the test piece and, when it is difficult to obtain the test piece having a width of 25 mm, the measurement maybe carried out on the basis of the test piece having an optional width and the measurement result may be converted into a tensile stress value to be obtained on the basis of the test piece having a width of 25 mm.

While the number of the second waist elastic members 32 as well as the intervals at which these elastic members are arranged in the front and rear waist regions 13, 14 may be appropriately selected depending on the desired tensile stress thereof, the tensile stress of the second waist elastic members 32 as a whole in the front waist region 13, i.e., the tensile stress of the lower elasticized regions 19A, 19B is preferably higher than the tensile stress of the upper elasticized region 18. It is for the reason that, in the front waist region 13, the liquid-absorbent structure 12 must be held in close contact with the wearer's body to prevent urine leak and, in the rear waist region 14, it is essential above all to assure an appropriate space adapted to retain discharged feces therein with the fitness of a degree sufficient to prevent leak of discharged feces. To ensure that the lower elasticized regions 19A, 19B have the tensile stress higher than the tensile stress of the upper elasticized region 18, the number of the elastic members may be increased in the front waist region 13 compared to the rear waist region 14 so far as the respective elastic members have the same tensile stress. If the number of the elastic members in the front waist region 13 is the same as the number of the elastic members, the elastic members each having the tensile stress higher than the tensile stress of the elastic members in the rear waist region 14 may be provided in the front waist region 13.

The components constituting the diaper 10 of the invention such as the inner and outer layer sheets 27, 28, the inner and outer sheets 41, 42, the respective members constituting the liquid-absorbent structure 12 and the respective elastic members 31, 32, 33, 54 maybe formed by those conventionally used in the relevant field used to make the disposable diaper. It is also possible to form the front member 21 and the intermediate member 23 of the chassis 11 by a continuous sheet or to form the chassis 11 by the front member 21 and the rear member 22 without incorporation of the intermediate member 23. While the pants-type disposable diaper 10 comprising the front and rear waist regions joined together along the respective pairs of opposite side edges are illustrated and described as the embodiment, the present invention is applicable not only to the pants-type diaper but also to the open-type diaper.

The invention claimed is:

1. A disposable diaper comprising:
   a chassis having a longitudinal direction, a transverse direction, a side configured to face a wearer's skin and a side configured to face away from a wearer's skin and configurationally comprising a front waist region, a rear waist region, a crotch region extending between said front and rear waist regions, a waist-opening and a pair of leg-openings,
   a liquid-absorbent structure provided on said side facing the wearer's skin of said chassis and extending across said crotch region further into said front and rear waist regions, said liquid-absorbent structure containing therein a liquid-absorbent core, and,
   a plurality of waist elastic members extending under tension in said transverse direction,
   said waist elastic members comprise first waist elastic members extending in a transverse direction in a vicinity of said waist-opening periphery and second waist elastic members provided between said leg-openings peripheries and said first waist elastic members and extending in said transverse direction across opposite lateral regions so as not to be present in central zones of said front and rear waist regions, and said second waist elastic members in said front waist region extend from each of transversely opposite side edges of said front waist region in said transverse direction beyond transversely opposite side edges of said liquid-absorbent core so as to cross said opposite side edges of said liquid-absorbent core without extending across said central zone of said front waist region while said second waist elastic members in said rear waist region extend from each of said transversely opposite side edges of said rear waist region in said transverse direction and terminate short of said side edges of said liquid-absorbent core.

2. The diaper according to claim 1, wherein a dimension in the transverse direction between said inner end portions of said second waist elastic members and said side edges of said liquid-absorbent core in said front waist region is in a range of about 10 to 30% of said dimension in the transverse direction of said liquid-absorbent core and said dimension in the transverse direction between inner end portions of said second waist elastic members and said side edges of said liquid-absorbent core in said front waist region is about 10% or less.

3. The diaper according to claim 1, wherein a rear end of said liquid-absorbent core is spaced from a region of the first waist elastic members closest to said rear end.

4. The diaper according to claim 1, wherein said chassis includes a sheet lying on a side of said second waist elastic members facing away from the wearer's skin and inner end portions of said second waist elastic members are permanently bonded to said sheet.

5. The diaper according to claim 4, wherein said sheet is formed of a moisture-permeable plastic film and has a thickness in a range of about 0.015 to 0.05 mm.

6. The diaper according to claim 2, wherein a rear end of said liquid-absorbent core is spaced from a region of the first waist elastic members closest to said rear end.

7. The diaper according to claim 2, wherein said chassis includes a sheet lying on a side of said second waist elastic members facing away from the wearer's skin and inner end portions of said second waist elastic members are permanently bonded to said sheet.

8. The diaper according to claim 3, wherein said chassis includes a sheet lying on a side of said second waist elastic members facing away from the wearer's skin and inner end portions of said second waist elastic members are permanently bonded to said sheet.

9. The diaper according to claim 6, wherein said chassis includes a sheet lying on a side of said second waist elastic members facing away from the wearer's skin and inner end portions of said second waist elastic members are permanently bonded to said sheet.

10. The diaper according to claim 7, wherein said sheet is formed of a moisture-permeable plastic film and has a thickness in a range of about 0.015 to 0.05 mm.

11. The diaper according to claim 8, wherein said sheet is formed of a moisture-permeable plastic film and has a thickness in a range of about 0.015 to 0.05 mm.

12. The diaper according to claim 9, wherein said sheet is formed of a moisture-permeable plastic film and has a thickness in a range of about 0.015 to 0.05 mm.

* * * * *